United States Patent
Saeki et al.

(10) Patent No.: US 10,905,341 B2
(45) Date of Patent: Feb. 2, 2021

(54) CANCER INVASIVENESS DIAGNOSIS SYSTEM

(71) Applicant: OSAKA CITY UNIVERSITY, Osaka (JP)

(72) Inventors: Souichi Saeki, Osaka (JP); Masatsugu Shiba, Osaka (JP)

(73) Assignee: OSAKA CITY UNIVERSITY, Osaka (JP)

( * ) Notice: Subject to any disclaimer, the term of this patent is extended or adjusted under 35 U.S.C. 154(b) by 544 days.

(21) Appl. No.: 15/743,210

(22) PCT Filed: Jul. 11, 2016

(86) PCT No.: PCT/JP2016/070460
§ 371 (c)(1),
(2) Date: Jan. 9, 2018

(87) PCT Pub. No.: WO2017/010461
PCT Pub. Date: Jan. 19, 2017

(65) Prior Publication Data
US 2018/0206741 A1 Jul. 26, 2018

(30) Foreign Application Priority Data
Jul. 10, 2015 (JP) .................. 2015-139114

(51) Int. Cl.
*A61B 5/026* (2006.01)
*A61B 5/00* (2006.01)
(Continued)

(52) U.S. Cl.
CPC ............ *A61B 5/0261* (2013.01); *A61B 1/018* (2013.01); *A61B 1/2736* (2013.01);
(Continued)

(58) Field of Classification Search
CPC ..... A61B 1/018; A61B 1/2736; A61B 5/0066; A61B 5/0073; A61B 5/0261; A61B 5/4238; A61B 5/6847; A61B 5/6852
See application file for complete search history.

(56) References Cited

U.S. PATENT DOCUMENTS

2012/0010494 A1   1/2012 Teramura

FOREIGN PATENT DOCUMENTS

JP   2010125272       6/2010
JP   2010220669 A    10/2010
(Continued)

OTHER PUBLICATIONS

Kishi et al., "Staging Laparoscopy Using ALA-Mediated Photodynamic Diagnosis Improves the Detection of Peritoneal Metastases in Advanced Gastric Cancer", Journal of Surgical Oncology, vol. 106, No. 3, 2012, pp. 294-298.
(Continued)

*Primary Examiner* — Michael T Rozanski
(74) *Attorney, Agent, or Firm* — Lando & Anastasi, LLP

(57) ABSTRACT

A cancer invasiveness diagnosis system includes an endoscope; a microtomography probe which is introduced into a body cavity together with the endoscope, the microtomography probe emitting a low-coherence light on a target tissue in which a target tumor is present to obtain an optical interference signal; a determination portion which is configured to obtain a tomography image of the target tissue including the target tumor and a blood flow velocity information in a blood vessel in the tomography image based on the optical interference signal, wherein the determination portion is configured to determine the cancer invasiveness of the target tumor based on the tomography image and the blood flow velocity information.

3 Claims, 15 Drawing Sheets

(51) Int. Cl.
*A61B 1/273* (2006.01)
*A61B 1/018* (2006.01)

(52) U.S. Cl.
CPC .......... *A61B 5/0066* (2013.01); *A61B 5/0073* (2013.01); *A61B 5/4238* (2013.01); *A61B 5/6847* (2013.01); *A61B 5/6852* (2013.01)

(56) References Cited

FOREIGN PATENT DOCUMENTS

JP      2014042842 A    3/2014
JP      2014104275 A    6/2014

OTHER PUBLICATIONS

International Search Report for application No. PCT/US2016/070460 dated Sep. 20, 2016.
International Search Report for application No. PCT/JP2016/070460 dated Sep. 20, 2016.

CANCER INVASIVENESS DIAGNOSIS SYSTEM

CROSS-REFERENCE TO RELATED APPLICATIONS

This application is a U.S. National Phase Application and claims the benefit under 35 U.S.C. § 371 of International Application No. PCT/JP2016/070460, filed Jul. 11, 2016, titled "CANCER INVASION DEPTH DIAGNOSIS SYSTEM," which claims priority from Japanese Patent Application No. 2015-139114, filed on Jul. 10, 2015, the entire contents of which are incorporated herein by reference in their entireties for all purposes.

BACKGROUND ART

If cancer is present in the gastrointestinal tract as an early-stage cancer, the risk of metastasis is low and part of such cancer can be endoscopically resected. On the other hand, in the case of advanced cancer, the risk of metastasis increases and the cancer is generally treated by surgical resection. In order to treat cancer in the gastrointestinal tract, it is important to exactly determine whether the cancer is in the early stage or advanced stage. Thus, a suitable evaluation of tumor invasiveness (a spreading degree in a thickness direction of the tissue) is a key factor.

As an example of an evaluation method for the invasiveness of the gastrointestinal cancer, a method using an image obtained by Narrow-Band Imaging (NBI) is known (for example, see Patent Document 1). In this method, based on the image obtained by the NBI method (an NBI image), the tumor invasiveness is evaluated by evaluating a distribution state of the blood vessels exclusively occurring in the tumor angiogenesis of the cancer.

CITATION LIST

Patent Document

[Patent Document 1]
Japanese Unexamined Patent Application, First Publication No. 2014-42842

SUMMARY OF INVENTION

Technical Problem

However, according to the method disclosed in Patent Document 1, it is not easy to determine whether the tumor has grown beyond the lamina muscularis mucosae from the image. Accordingly, for example, a suitable diagnosis rate of the cancer invasiveness for gastric cancer based on the NBI image nowadays is less than 70%, and thus there is still room for improvement.

The present invention has been made in view of the above circumstances and an object of the present invention is to provide a cancer invasiveness diagnosis system having high accuracy in diagnosing the cancer invasiveness.

Solution to Problem

The present invention relates to a cancer invasiveness diagnosis system including an endoscope; a microtomography probe which is introduced into a body cavity together with the endoscope, the microtomography probe emitting a low-coherence light on a target tissue in which a target tumor is present to obtain an optical interference signal; a determination portion which is configured to obtain a tomography image of the target tissue having the target tumor and blood flow velocity information in a blood vessel in the tomography image based on the optical interference signal, wherein the determination portion is configured to determine the cancer invasiveness of the target tumor based on the tomography image and the blood flow velocity information.

The determination portion may specify connected angiogenic blood vessels which are communicated with pre-existing blood vessels in a submucosa layer or a muscularis propria layer among angiogenic blood vessels of the target tumor based on the tomography image and the blood flow velocity information, and the determination portion may determine the cancer invasiveness of the target tumor based on an evaluation result of the connected angiogenic blood vessels.

The microtomography probe may emit low-coherence light that is high-frequency modulated.

The blood flow velocity information may include information relating to an initial rise of the blood flow velocity due to the recovery of a blood flow after the blood vessel is pressed and the blood flow velocity in the blood vessel becomes equal to or lower than a predetermined value.

Advantageous Effects of Invention

According to the cancer invasiveness diagnosis system of the present invention, it is possible to diagnose the cancer invasiveness with a high level of accuracy.

DESCRIPTION OF EMBODIMENTS

A first embodiment of the present invention will be described by referring FIGS. 1 to 6. Firstly, the principle of the cancer invasiveness evaluation of the present invention will be described.

Figure 1:
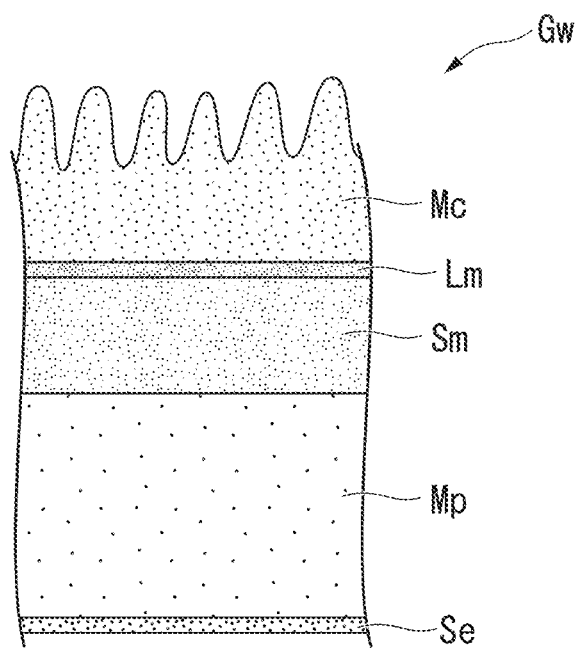
FIG. 1 is a schematic view showing a cross section of gastric walls.

FIG. 1 is a schematic view showing a cross section of gastric walls. The gastric walls Gw has a structure formed of a mucosa layer Mc, a lamina muscularis mucosae Lm, a submucosa layer Sm, a muscularis propria layer Mp, and a serosa Se in this order from an inner cavity side of the stomach. According to the "Japanese Classification of Gastric Carcinoma (14th Edition)" edited by the Japanese Gastric Cancer Association, the cancer recognized as a tumor formed by a mass of cancerous cells is classified to a lowest invasiveness T1 in a situation in which the tumor is confined until the submucosa layer Sm and the tumor does not invade the muscularis propria layer Mp. According to the "Japanese Gastric Cancer Treatment Guidelines 2014 (4th Edition)" edited by the Japanese Gastric Cancer Association, an endoscopic treatment is only applicable to a situation in which the tumor is confined in the mucosa layer Mc among the lesions with an invasiveness T1, and in a case in which the tumor has invaded the submucosa layer, a surgical operation is applicable.

Accordingly, in order to determine whether the endoscopic treatment or the surgical operation is applicable to the tumor as a treatment target, it is mostly preferable to acquire information regarding whether the tumor has invaded beyond the lamina muscularis mucosae Lm. However, based on a tomography image of the gastric walls, a means for non-invasively and clearly observing the lamina muscularis mucosae Lm in real time is unavailable nowadays, thus it is difficult to determine whether the tumor has invaded beyond the lamina muscularis mucosae Lm and reached the submucosa layer Sm by a non-invasive means and in real time.

The inventors propose a whole new approach to evaluate the cancer invasiveness in the gastric walls instead of observing the lamina muscularis mucosae.

The tumor formed of a mass of cancerous cells uses angiogenic blood vessels inside the tumor itself or surrounding the tumor itself to help the tumor grow. A network constructed by such angiogenic blood vessels formed inside the tumor or surrounding the tumor becomes dense together with the tumor growth.

Figure 2:
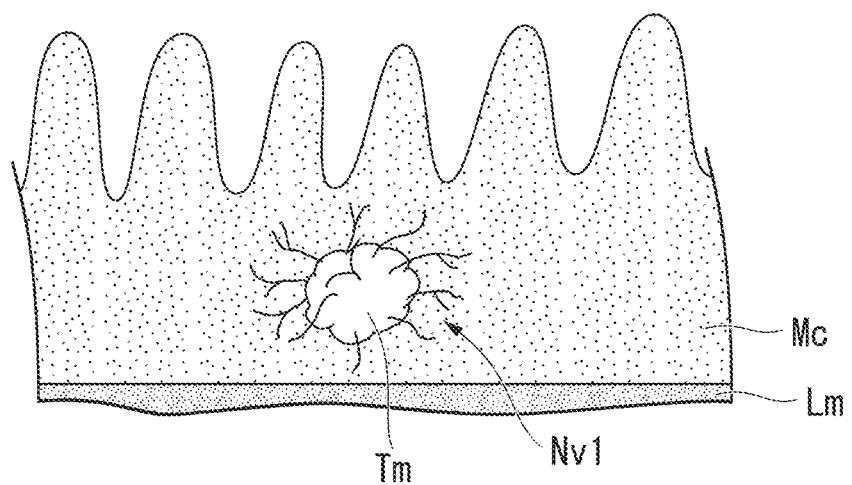
FIG. 2 is a view showing the mucosa layer and the tumor.

As shown in FIG. 2, in an early stage of the tumor Tm present in the mucosa layer Mc, the tumor forms angiogenic blood vessels Nv1 surrounding the tumor itself. The angiogenic blood vessels Nv1 communicate with the pre-existing capillaries in the mucosa layer Mc for draining blood to the tumor Tm so as to supply the oxygen and nutrients to the tumor Tm.

Figure 3:
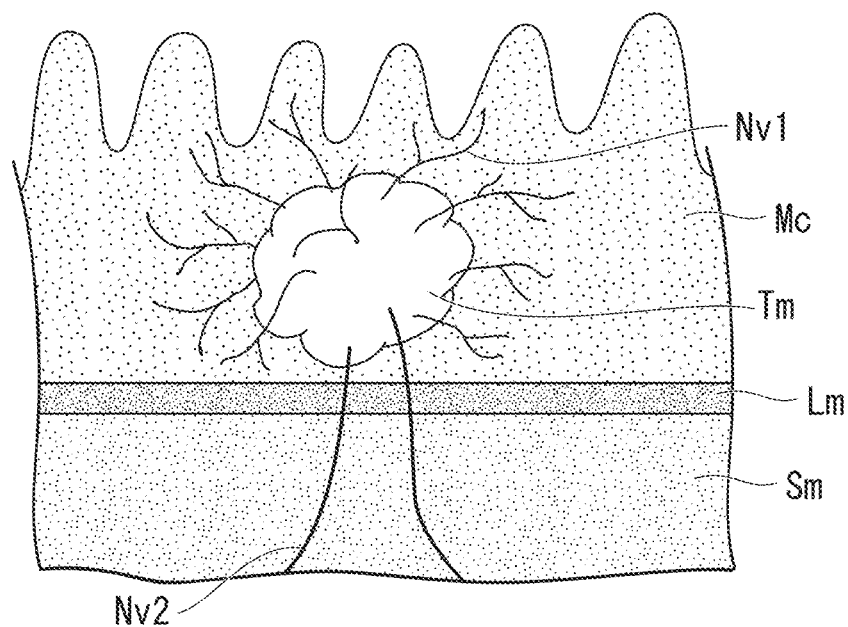
FIG. 3 is a view showing the mucosa layer and the tumor.

When the tumor Tm has grown to be a certain size, acquiring the necessary oxygen and nutrients only from the capillaries in the mucosa layer Mc becomes insufficient. Accordingly, as shown in FIG. 3, the tumor Tm forms other angiogenic blood vessels Nv2 beyond the lamina muscularis mucosae Lm for attempting to communicate with pre-existing blood vessels having a larger inner diameter in the submucosa layer Sm or the muscularis propria layer Mp. For example, as disclosed in Kishi K, et al., Journal of Surgical Oncology, 106 (3): 294-298, 2012, it is reported that a fluorescence materiel introduced into the gastric vein is incorporated into the tumor existed in the gastric mucosa. Such a report can be recognized as proof of the existence of the angiogenic blood vessels Nv2.

When the angiogenic blood vessels Nv2 communicate with the existed blood vessels in the submucosa layer Sm or the muscularis propria layer Mp, more blood flows into the angiogenic blood vessels Nv2 than that of the formed angiogenic blood vessels Nv1. As a result, the blood flow velocity in the angiogenic blood vessels Nv2 is faster than the blood flow velocity in the angiogenic blood vessels Nv1, and the blood flow velocity in the angiogenic blood vessels Nv2 exceeds a predetermined value.

Such a situation in which the angiogenic blood vessels Nv2 are communicated with the pre-existing blood vessels in the submucosa layer Sm or the muscularis propria layer Mp, means that the tumor Tm has grown to a degree such that the tumor Tm will soon grow beyond the lamina muscularis mucosae Lm, or the tumor Tm has already grown to a degree such that the tumor Tm will soon grow beyond the lamina muscularis mucosae Lm. The inventors found that it is possible to determine whether the tumor as the treatment target is applicable for the endoscopic treatment by evaluating the blood flow velocity in the angiogenic blood vessels in the mucosa layer Mc rather than directly observing the lamina muscularis mucosae.

The capillaries in both of the mucosa layer Mc and the angiogenic blood vessels formed by the tumor are microvessels with an inner diameter in the order of microns. However, it is possible to obtain an image including information regarding the blood flow velocity in the angiogenic blood vessels by a visible microtomography system using low-coherence light.

The cancer invasiveness diagnosis system of the present embodiment will be described below.

Figure 4:
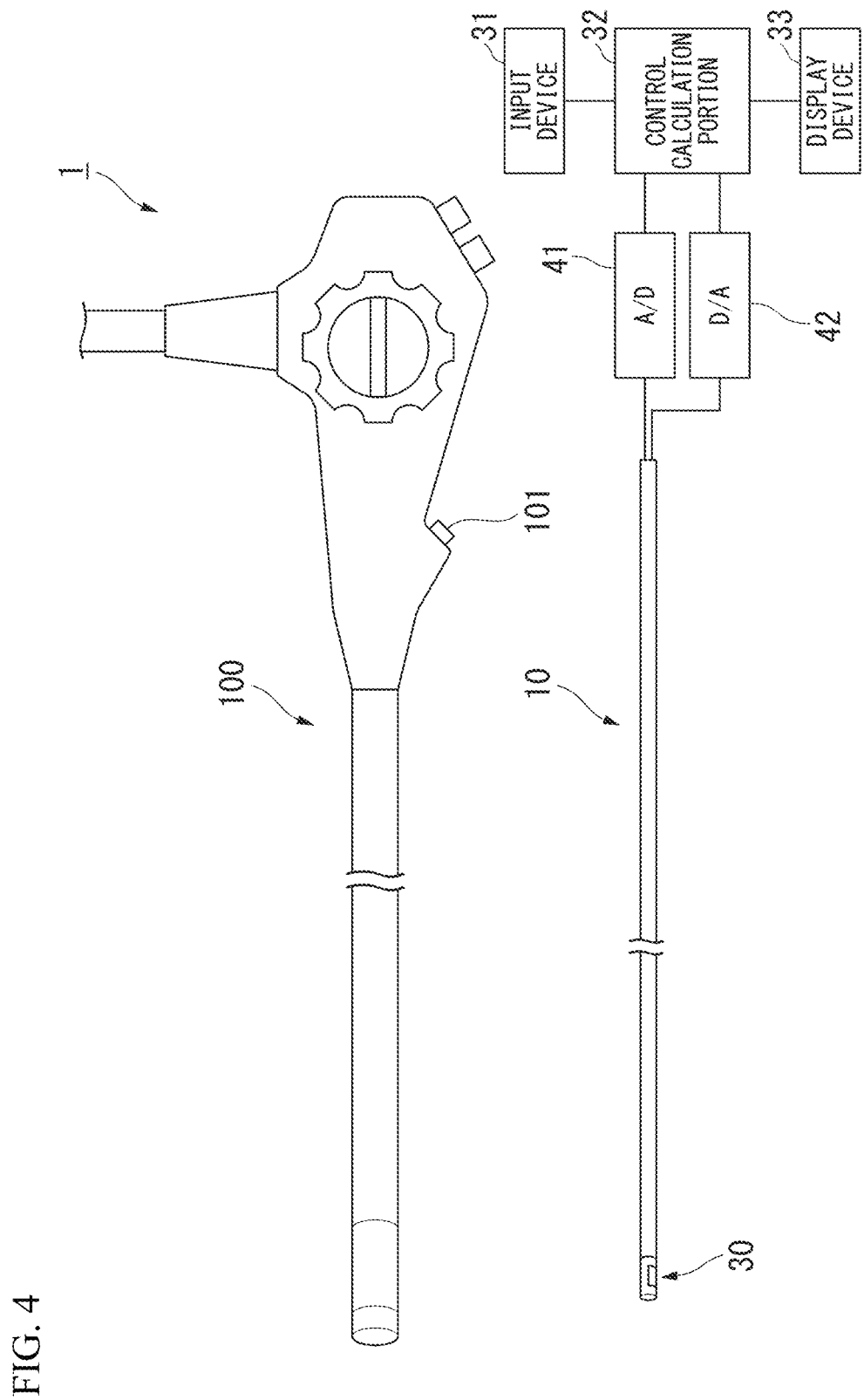
FIG. 4 is a view showing the overall configuration of the cancer invasiveness diagnosis system according to a first embodiment of the present invention.

FIG. 4 is a view showing an overall configuration of the cancer invasiveness diagnosis system. A cancer invasiveness diagnosis system 1 includes an endoscope 100, and a microtomography probe 10 which is inserted into a channel of the endoscope 100 to be introduced into a body cavity together with the endoscope 100. As an example of the endoscope 100, various well-known endoscopes capable of performing optical observations can be suitably selected and used.

Figure 5:
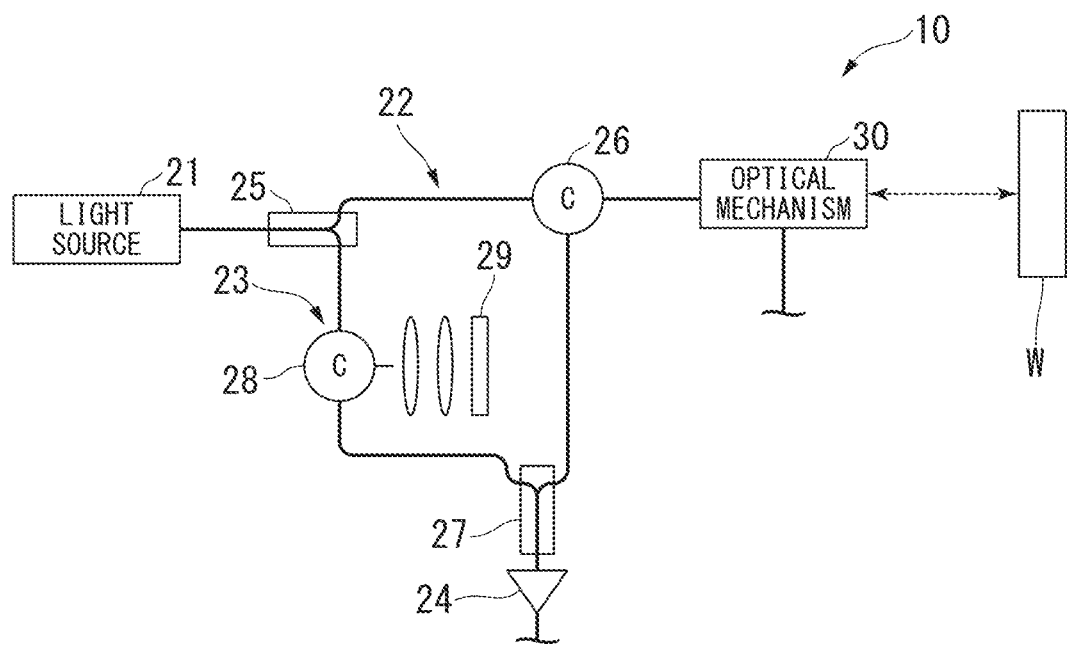
FIG. 5 is a schematic view showing a mechanism of a microtomography probe in the cancer invasiveness diagnosis system.

FIG. 5 is a schematic view showing a mechanism of the microtomography probe 10. The microtomography probe 10 includes a light source 21, an object arm 22, a reference arm 23, and an optical detector 24. The optical elements of the microtomography probe 10 are connected with each other by optical fiber.

Light emitted by the light source 21 is split by a coupler (a beam splitter) 25. An aspect of the split light is guided by the object arm 22 to be an object light, and the other aspect of the split light is guided by the reference arm 23 to be a reference light.

The object arm 22 includes a circulator 26 and an optical mechanism 30 for outputting the object light to a measurement target. The object light guided by the object arm 22 is guided to the optical mechanism 30 via the circulator 26, thus irradiating a measurement object W. The object light is reflected at both of a surface of the object W and a cross section of the object W as backscattering light, returned to the circulator 26, and guided to a coupler 27.

The optical mechanism 30 includes optical fibers (not shown), a driving portion, and a light rotary joint, and the basic configuration of the optical mechanism 30 is well-known. The optical mechanism 30 can emit the object light to the measurement object W while scanning the object light by using the driving portion to rotate the optical fibers. As an example, a rotary actuator can be used as the driving portion.

The reference arm 23 includes a circulator 28 and a reflection mirror 29. The reference light guided by the reference arm 23 is guided via the circulator 28, through a collimating lens, a condensing lens and the like, and finally guided to the reflection mirror 29. The reference light reflected by the reflection mirror 29 is returned to the circulator 28 and guided to the coupler 27. In other words, the object light and the reference light are multiplexed (superimposed) at the coupler 27 and a generated interference light is detected by the optical detector 24.

A galvanometer mirror, a resonant mirror, and the like can be used as the reflection mirror 29. When the resonant mirror is utilized, it is possible to obtain the tomography at a high speed. In the situation of utilizing the resonant mirror, a curved mirror having a reflecting surface curved in a concave shape may be disposed between the collimating lens and the resonant mirror.

As shown in the FIG. 4, the microtomography probe 10 is connected with an input device 31, a control calculation portion (determination portion) 32, and a display device 33. The input device 31 is a device for inputting various settings and operation input to the driving portion of the optical mechanism 30 by the user, and a configuration of the input device is not specifically limited. The control calculation portion 32 controls an operation of the microtomography probe 10 by generating and transmitting an instruction signal to each portion of the microtomography probe 10 based on the operation input to the input device 31. Also, the control calculation portion 32 performs various calculations and processing of an optical interference signal received from the optical detector 24, acquires the tomographic image data (tomography) and various information of the measurement target W, and makes a judgement according to a predetermined standard based on the tomographic image data. The display device 33 displays the image and the various information acquired by the control calculation portion 32.

The interference light multiplexed at the coupler 27 is input to the optical detector 24. The optical detector 24 detects this as an optical interference signal (a signal indicating an intensity of the interference light). The analog optical interference signal output from the optical detector 24 is converted to a digital signal at an A/D converter 41 (see FIG. 4), and the converted digital signal is input to the control calculation portion 32. The digital instruction signal transmitted from the control calculation portion 32 is converted to an analog signal at a D/A converter 42, and the converted analog instruction signal is input to the optical mechanism 30.

The microtomography probe 10 does not only acquire the microtomography by Optical Coherence Tomography (OCT), but also acquires information relating to the velocity of the matter shown by the tomography. The details will be described below.

An operation of the cancer invasiveness diagnosis system 1 having the above-mentioned configuration according to the present embodiment when being used will be described below.

Firstly, the user inserts the endoscope 100 from a mouth of a patient, and the user introduces a distal end portion thereof into the gastrovascular cavity. The user uses the endoscope 100 to observe the gastrovascular cavity while determining a position of the target tumor which is a treatment target of the invasiveness diagnosis, and the user moves the distal end portion thereof to the vicinity of the target issues at which the target tumor exists.

Subsequently, the user inserts the microtomography probe 10 from a forceps port 101 of the endoscope 100 to introduce the microtomography probe 10 into a channel (not shown) of the endoscope 100. Next, the user controls the optical mechanism 30 disposed at a distal end of the microtomography probe 10 to protrude from the endoscope 100. The microtomography probe 10 may be inserted into the endoscope 100 before the endoscope is introduced into the gastrovascular cavity.

Figure 6:
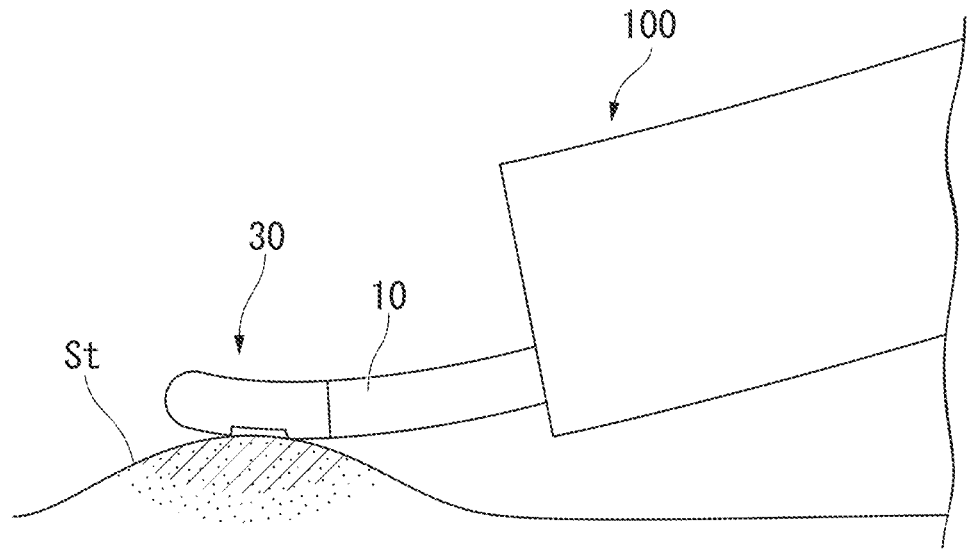
FIG. 6 is a view showing the cancer invasiveness diagnosis system in operation.

As shown in FIG. 6, the user puts an emission surface of the microtomography probe 10 in a direction facing the target tissue St, and makes the object light to be emitted toward the target tissue St. The object light may be emitted when the microtomography probe 10 is in contact with the surface of the target tissue St, and the object light may be emitted when the microtomography probe 10 and the surface of the target tissue St is slightly spaced from each other. The emitted object light is reflected at both of the surface of the target tissue St and the inside of the target tissue St, part of the reflected light is returned to the microtomography probe 10. Information relating to several slices of the tomography of the target tissue St including the target tumor can be continuously acquired by driving the optical mechanism 30.

The optical interference signal detected by the optical detector 24 is processed by a predetermined processing such as a Short-time Fast Fourier Transform (ST-FFT) and the like, and then the transformed signal is transmitted to the control calculation portion 32. In the control calculation portion 32, an OCT tomography image of the target tissue St including the target tumor is generated based on the intensity of the received optical interference signal, while a flow velocity distribution of the moving matters in the tomography image is generated by using a Doppler modulation frequency detected based on the frequency analysis. Accordingly, information relating to the blood flow velocity in each blood vessel in the tomography image (blood flow velocity information) can be acquired by obtaining a flow velocity distribution of the red blood cells in the blood vessel.

After the tomography image and the flow velocity distribution are generated, the control calculation portion 32 determines the cancer invasiveness of the target tumor based on the tomography image and the blood flow velocity information automatically or in accordance with an instruction from the user. As described above, a basic principle of the determination is to specify and evaluate the angiogenic blood vessels Nv2 (hereinafter referred as "connected angiogenic blood vessels") communicated with the pre-existing blood vessels in the submucosa layer Sm or the muscularis propria layer Mp based on the blood flow velocity information. A threshold value of the blood flow velocity for specifying the connected angiogenic blood vessels, for example, can be determined to a value of 1 mm per second. The specification of the connected angiogenic blood vessels may be performed by using a combination of the blood flow velocity information and a diameter of the blood vessel obtained from the tomography image. Generally, the angiogenic blood vessels Nv2 have diameters larger than that of the angiogenic blood vessels Nv1 such that the accuracy of the specification of the connected angiogenic blood vessels can be further improved.

The evaluation standard of the specified connected angiogenic blood vessels is not limited to one type. For example, various types of evaluation standards may be selected, including, for example, a maximum value, a minimum value, and an average value in several tomography images.

Existence of connected angiogenic blood vessels
Number of connected angiogenic blood vessels
Area or area ratio in the tomography image of the connected angiogenic blood vessels
Flow rate (multiplication of flow velocity and cross section area) of the connected angiogenic blood vessels in the tomography image The control calculation portion 32 determines the cancer invasiveness of the target tumor according to the selected evaluation standard, and displays the result on the display device 33. A standard combining the evaluation standard and the cancer invasiveness, a standard relating to the stage of the cancer invasiveness and the like can be suitably set by the user using the input device 31. The cancer invasiveness may be evaluated by a combination of multiple evaluation standards.

As described above, according to the cancer invasiveness diagnosis system 1 of the present embodiment, the tomography images of the target tissue including the target tumor and the blood flow velocity information in the tomography images can be obtained according to the optical interference signal of the target tissue including the target tumor, wherein the optical interference signal is obtained by the microtomography probe 10. Thus, the control calculation portion 32 evaluates the state of the connected angiogenic blood vessels in the tomography images based on the obtained tomography images and the blood flow velocity information, thus the control calculation portion 32 determines the cancer invasiveness of the target tumor according to the evaluation result.

Accordingly, in parallel with the observation of the target tissues by using the optical endoscope, the cancer invasiveness of the target tumor can be determined with a high level of accuracy and in real time. As a result, it is possible to quickly determine whether or not the target tumor is suitable for endoscopic treatment, such that an appropriate treatment can be performed while keeping the amount of stress of a patient to a minimum.

The diagnosis can be made using a two-dimensional image such that an artifact due to a body motion of the patient and the peristalsis of an organ can be suitably removed.

Further, the cancer invasiveness diagnosis system 1 can three-dimensionally visualize the network of the capillaries in the gastric mucosa, including the angiogenic blood vessels of the tumor, using a convention method. The information of the capillaries network is generally qualitative information; however, according to the cancer invasiveness diagnosis system 1, a diagnosis with a higher level of accuracy can be made by combining the information of the capillaries network with quantitative information such as the above-described tomography image and the blood flow velocity information. For example, the connected angiogenic blood vessels can be specified by using a position and a blood flow velocity in the capillaries network.

In a convention capillaries network image obtained by using the Magnifying Endoscopy with the NBI, blood vessels positioned at different depths are indicated in a superimposed fashion. In the cancer invasiveness diagnosis system 1, the information of the three-dimensional capillaries network including the depth directional information can be obtained. Accordingly, by combining the information of the three-dimensional capillaries network and the blood flow velocity information, a volume of blood supplied from the connected angiogenic blood vessels to the target tumor can be calculated by inverse analysis using numerical analysis method based on fluid mechanics. The fact that much blood is supplied from the connected angiogenic blood vessels to the target tumor indicates that proliferation of the cancerous cells in the target tumor is actively performed. Accordingly, it is possible to control the control calculation portion 32 to calculate the cancer invasiveness and the metastasis risk (possibility of the target tumor metastasis) in a higher accuracy.

As shown in FIG. 5, a configuration example based on Swept-Source Optical Coherence Tomography (SS-OCT) which is a kind of Fourier Domain Optical Coherence Tomography is shown. Instead of this, Spectral-Domain Optical Coherence Tomography (SD-OCT) may be used.

Next, a second embodiment of the present invention will be described by referring to FIGS. 7 to 8. In the following description, the same reference numerals will be given to configurations which are common to those which are previously described, and thus, a repeated description will be omitted.

Figure 7:
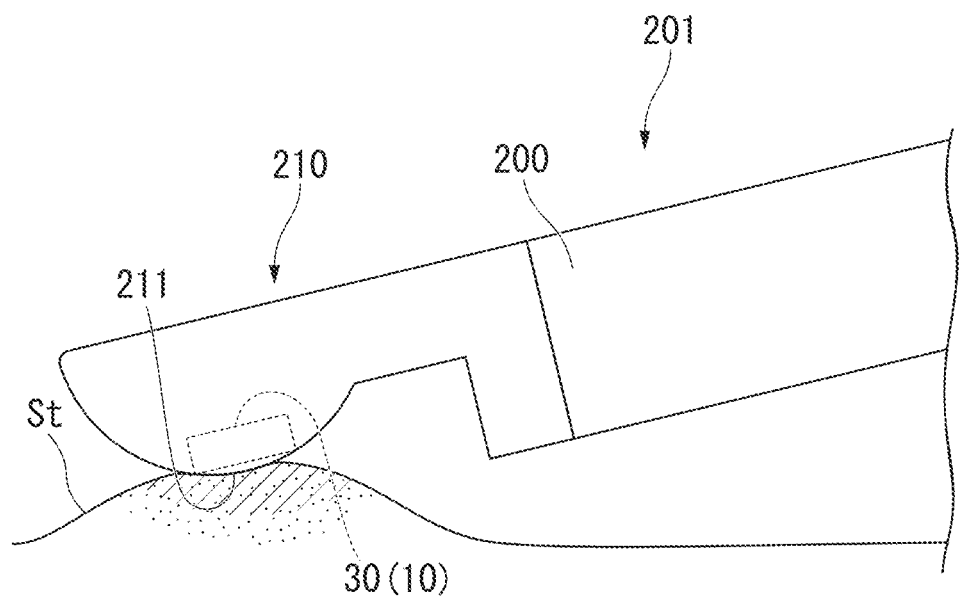
FIG. 7 is a view showing a distal end portion of an endoscope of the cancer invasiveness diagnosis system according to a second embodiment of the present invention.
Figure 8:
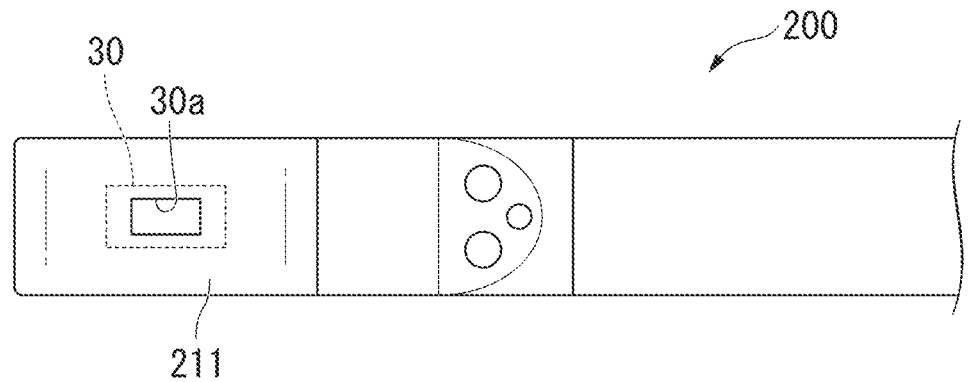
FIG. 8 is a view showing the distal end portion from a different direction.

FIG. 7 is a view showing a distal end portion of an endoscope 200 of the cancer invasiveness diagnosis system 201 according to the present embodiment. In the cancer invasiveness diagnosis system 201, the microtomography probe 10 is disposed inside the endoscope 200 rather than disposes inside the channel of the endoscope 200 such that the endoscope and the microtomography probe are configured to be integrated. The optical mechanism 30 is disposed inside a probe portion 210, wherein the probe portion 210 is disposed at a distal end portion of the endoscope 200, and the optical mechanism 30 is configured to emit the object light to the target tissue. As shown in FIG. 8, an emission port 30a of the optical mechanism 30 from which the object light is emitted is covered by a transparent member, and a pressing surface 211 is formed at the emission port 30a and the vicinity of the emission port 30a, wherein the pressing surface 211 is configured for pressing the tissue in contact therewith.

An operation of the cancer invasiveness diagnosis system 201 having the above-mentioned configuration when being used will be described below. Firstly, in a state in which the pressing surface 211 is slightly in contact with the target tissue St, the user obtains the blood flow velocity information in each blood vessel in the OCT tomography image and the tomography image and specifies the positions of the connected angiogenic blood vessels. The tomography image and the blood flow velocity information are stored in the control calculation portion 32, built-in storage medium (not shown), and the like.

Subsequently, the user operates the endoscope 200 to press the target tissue St by the pressing surface 211 while confirming the blood flow velocity in the connected angiogenic blood vessels. When the blood flow velocity in the connected angiogenic blood vessels is equal to or lower than a predetermined value (for example, 1 mm per second) such that ischemia occurs, the user operates the endoscope 200 to cancel the pressing to the target tissue by the pressing surface 211. Once the pressing to the target tissue is canceled, blood flow in each blood vessel of the target tissue recovers and the blood flow velocity increases again. The change of the blood flow velocity due to the recovery of the blood flow is sequentially obtained by the control calculation portion 32. Accordingly, the control calculation portion 32 can obtain the initial rise of the blood flow velocity (a slope of increase rate) due to the recovery of the blood flow as one of the blood flow velocity information in each blood vessel in the tomography image.

The information related to the initial rise of the blood flow velocity due to the recovery of the blood flow after the ischemia can be utilized for the cancer invasiveness determination by the control calculation portion 32 in various aspects. For example, the accuracy of specifying the connected angiogenic blood vessels may be improved by combining the maximum blood flow velocity and the initial rise of the blood flow velocity, and in order to determine the cancer invasiveness of the target tumor, the initial rise of the blood flow velocity may be considered as one of the evaluation standards and be used individually or together with other evaluation standards.

According to the cancer invasiveness diagnosis system 201 according to the present embodiment, as the same with the cancer invasiveness diagnosis system 1 according to the first embodiment, it is possible to determine the cancer invasiveness of the target tumor in real time.

The control calculation portion 32 can obtain the information relating to the initial rise of the blood flow velocity due to the recovery of the blood flow after the blood flow velocity in each blood vessel becomes equal to or lower than a predetermined value, as one of the blood flow velocity information, the accuracy of specifying the connected angiogenic blood vessels and the accuracy of determining the cancer invasiveness of the target tumor can be improved.

The endoscope 200 and the microtomography probe 10 are integrated, thus the broad pressing surface 211 can be provided in the surrounding of the emission port 30a. As a result, the operation of pressing the tissue for causing the connected angiogenic blood vessels to become ischemia can be suitably performed. Additionally, it is not necessary to insert and remove the microtomography probe such that a system with superior maneuverability can be realized.

Preferred embodiments of the present invention have been described. However, the scope of the present invention is not limited to the above-mentioned embodiments thereof. Additions, omissions, substitutions, and other modifications of configurations can be made without departing from the spirit or scope of the present invention.

For example, in the above-described examples, the example of obtaining the blood flow velocity information by the frequency analysis using the ST-FFT processing and the like, and detecting the Doppler modulation frequency due to the blood flow, is described. However, by configuring the cancer invasiveness diagnosis system in which high-frequency modulated low-coherence light is emitted from the microtomography probe, the blood flow velocity information can be obtained in a higher accuracy. The high-frequency modulation can be performed by using a conventional Electro-Optical Modulator (EOM), an Acousto-Optical Modulator (AOM), or the like. In a case in which high-frequency modulation is performed, a configuration using Time-Domain Optical Coherence Tomography (TD-OCT) is preferable.

It is possible to significantly improve the resolution of the blood flow velocity information by performing processing including Hilbert transformation to the interference signal obtained from the high-frequency modulated low-coherence light. Specifically, an analytic signal is created by treating the interference signal as the real part, and shifting the phase of the interference signal by 90 degrees to obtain the imaginary part. By determining an amplitude and the phase using the analytic signal, and furtherly determining the Doppler modulation frequency based on the amplitude and the phase, it is possible to calculate the blood flow velocity with a higher level of accuracy to obtain the blood flow velocity information. The blood flow velocity in the capillaries is not so high. Since the detection accuracy in the low-velocity range is significantly improved by increasing the resolution of the blood flow velocity, the acquisition accuracy of the blood flow velocity information in the capillaries can be significantly improved. As a result, the accuracy of the cancer invasiveness and the metastasis risk calculated by the determination portion is further improved.

In addition, it is possible to reduce the common-phase noise by referring to nearby phase information in the interference signal using nearby autocorrelation together. As a result, it is possible to furtherly improve the resolution of the blood flow velocity information. In a case where the nearby autocorrelation is used, it is not necessary to use the EOM; however, there is a merit that detection of a high-frequency band is realizable by using the EOM.

In a study by the inventors, specifically in an in vitro study using an intralipid solution as a Newtonian fluid and a red blood cell suspension, due to introduction of the method of nearby autocorrelation, the detection of micro-scale flow with a flow velocity equal to or lower than 500 micron meters per second, and a detection of blood rheology characteristic in a micro-scale flow with a flow velocity equal to or lower than 500 micron meters per second were successful. Further, in an in vivo study using Oryzias latipes, due to introducing the method of nearby autocorrelation, a visualization of a three-dimensional microtomography image with a spatial resolution in a range from 5 micron meters to 25 micron meters, and a visualization of a microtomography image of a three-dimensional Doppler frequency distribution are successful, also, a detection of the Doppler frequency due to blood vessels pulse becomes possible.

Due to the above-described change of the algorithm, the accuracy of specifying the connected angiogenic blood vessels and the accuracy of the information relating to the connected angiogenic blood vessels are furtherly improved such that the determination accuracy of the cancer invasiveness of the target tumor can be furtherly improved.

Figure 9:
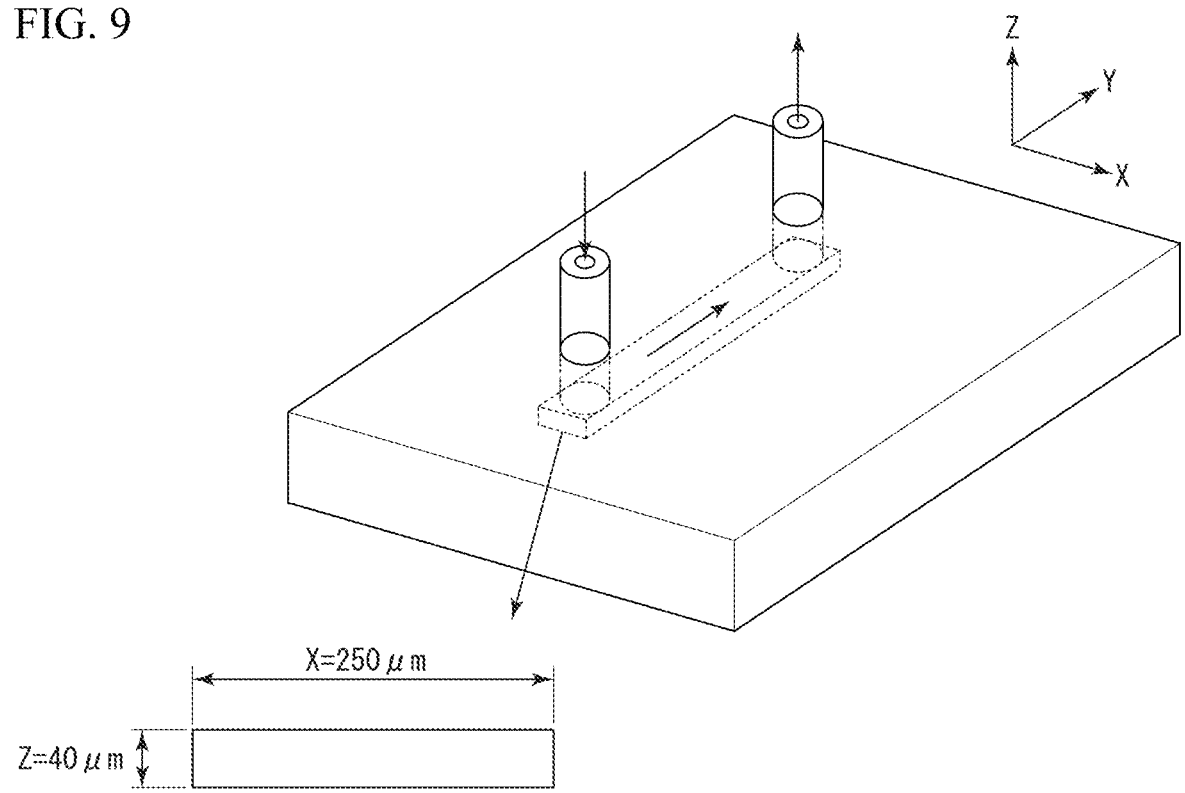
FIG. 9 is a view showing the structure of a test flow path.

FIG. 9 is a view showing the structure of a test flow path used in the study using the intralipid solution and the red blood cell suspension. The flow path has a dimension of 250 micron meters in the X axis direction and a dimension of 40 micron meters in the Z axis direction, which are set by assuming dimensions of the human capillaries.

Figure 10A:
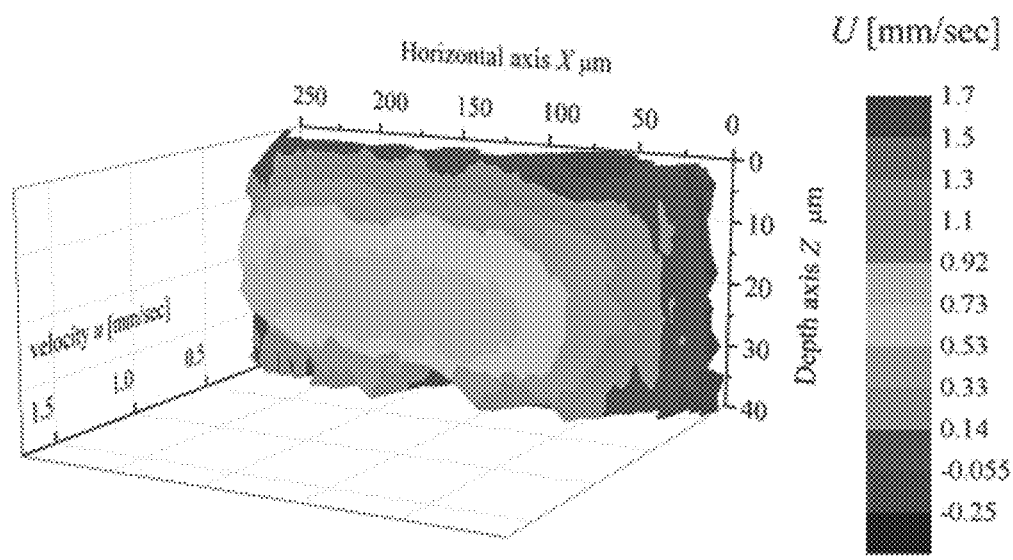
FIG. 10A is a view showing a three-dimensional blood flow velocity tomographic distribution image in a study using an intralipid solution.
Figure 10B:
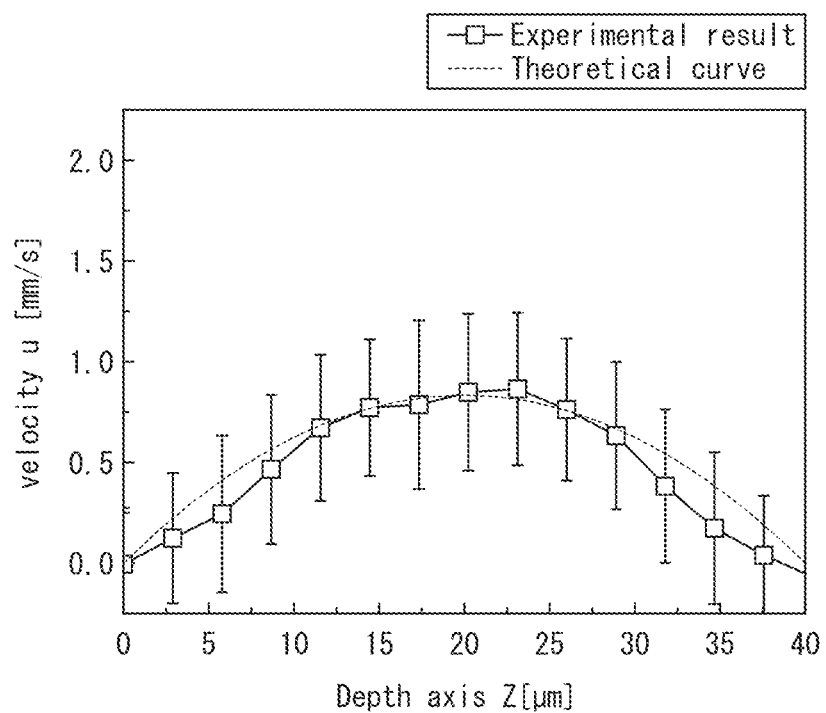
FIG. 10B is a view showing a blood flow velocity distribution graph by extracting a part of the three-dimensional blood flow velocity tomographic distribution image shown in FIG. 10A.

In FIG. 10A to FIG. 11B, measurement results using the intralipid solution are shown. In FIG. 10A and FIG. 10B, measurement results obtained in a condition that an average flow velocity is 0.5 micro meters per second are shown. FIG. 10A is a three-dimensional blood flow distribution tomography image, and FIG. 10B is a graph extracted from the three-dimensional blood flow distribution tomography image, showing a flow velocity distribution only at a position where X is 125 micron meters. In the present study, a bias error is 72 micron meters per second, and a dispersion error is 352 micron meters per second.

Figure 11A:
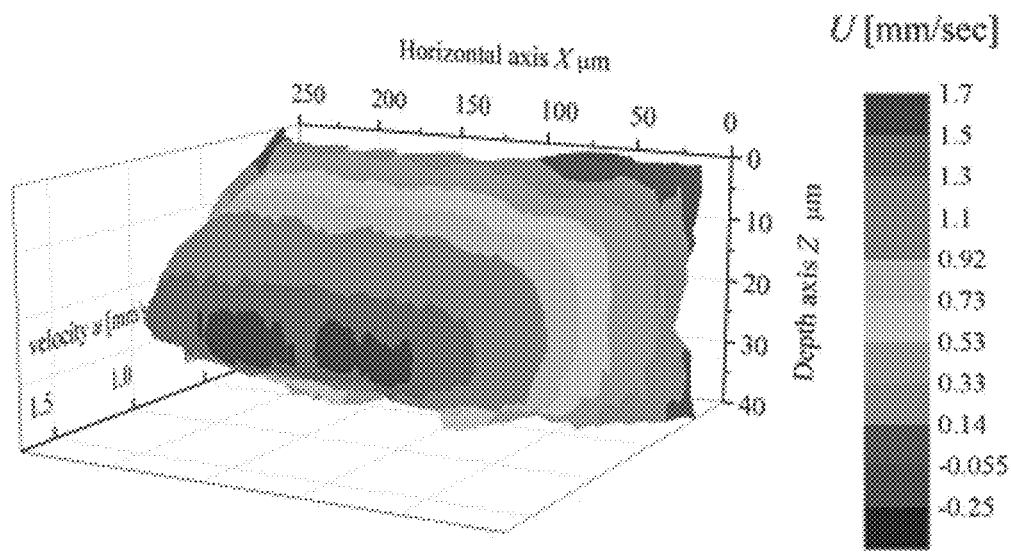
FIG. 11A is a view showing a three-dimensional blood flow velocity tomographic distribution image in a study using an intralipid solution.
Figure 11B:
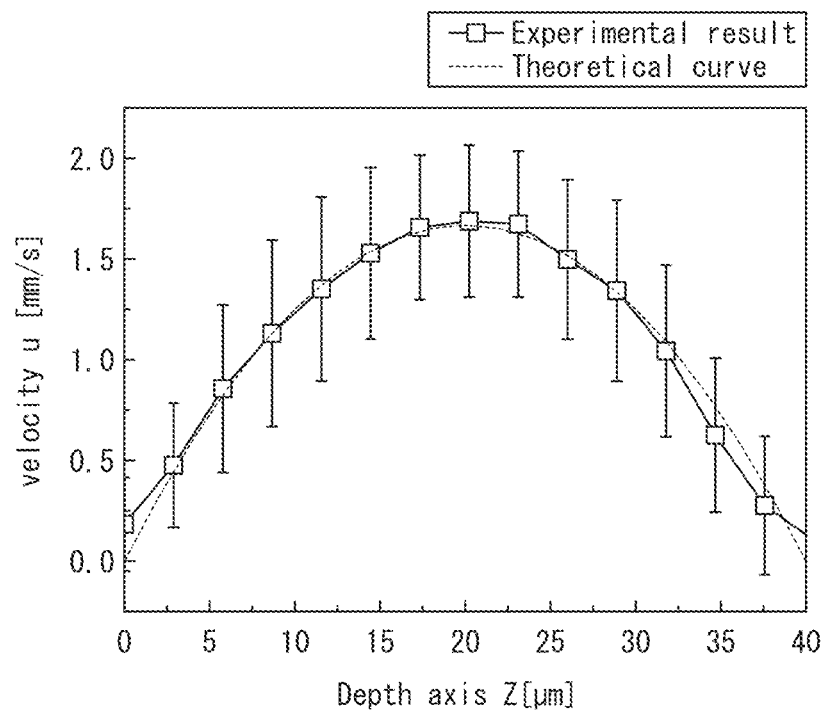
FIG. 11B is a view showing a blood flow velocity distribution graph by extracting a part of the three-dimensional blood flow velocity tomographic distribution image shown in FIG. 11A.

In FIG. 11A and FIG. 11B, measurement results obtained in a condition that an average flow velocity is 1.0 micro meter per second are shown. FIG. 11A is a three-dimensional blood flow distribution tomography image, and FIG. 11B is a graph extracted from the three-dimensional blood flow distribution tomography image, showing a flow velocity distribution only at a position where X is 125 micron meters. In the present study, a bias error is 57 micron meters per second, and a dispersion error is 385 micron meters per second. In the study using the intralipid solution, a detection of the flow velocity with a measurement precision of 13.4 micro meters per second in an optical axis direction (Y axis direction) is realized.

Figure 12A:
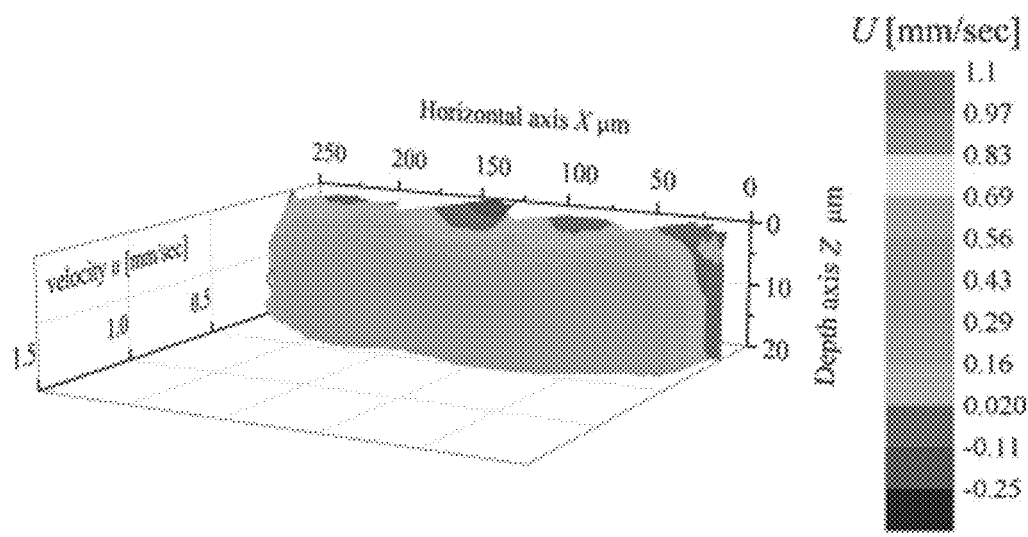
FIG. 12A is a view showing a three-dimensional blood flow velocity tomographic distribution image in a study using a red blood cell suspension.
Figure 12B:
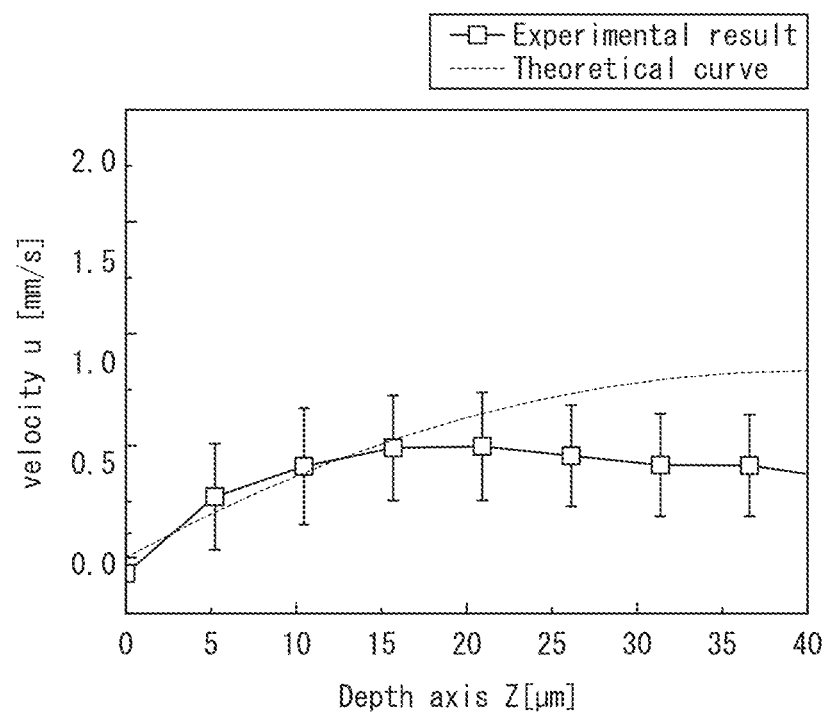
FIG. 12B is a view showing a blood flow velocity distribution graph by extracting a part of the three-dimensional blood flow velocity tomographic distribution image shown in FIG. 12A.

In FIG. 12A to FIG. 13B, measurement results using a red blood cell suspension (Hct 40%) are shown. In FIG. 12A and FIG. 12B, measurement results obtained in a condition that an average flow velocity is 0.5 micro meters per second are shown. FIG. 12A is a three-dimensional blood flow distribution tomography image, and FIG. 12B is a graph extracted from the three-dimensional blood flow distribution tomography image, showing a flow velocity distribution only at a position where X is 125 micron meters. In the present study, a dispersion error is 201 micron meters per second.

Figure 13A:
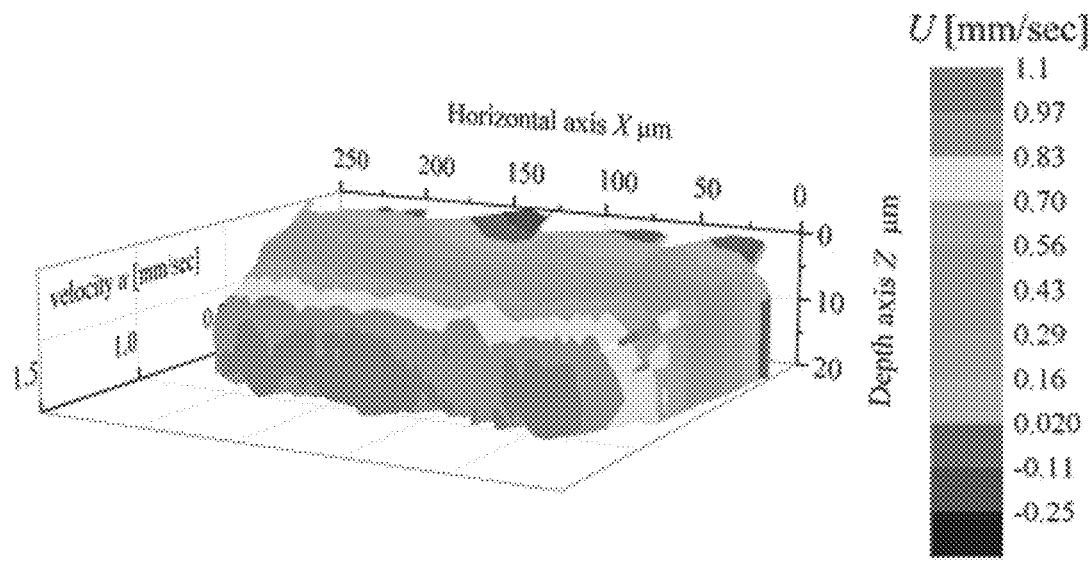
FIG. 13A is a view showing a three-dimensional blood flow velocity tomographic distribution image in a study using a red blood cell suspension.
Figure 13B:
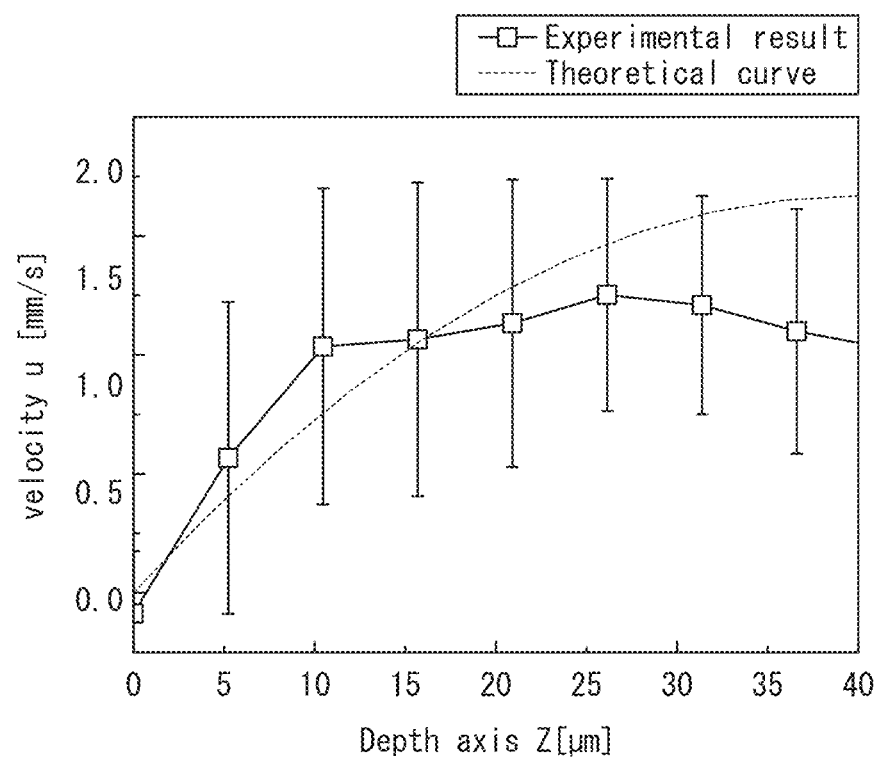
FIG. 13B is a view showing a blood flow velocity distribution graph by extracting a part of the three-dimensional blood flow velocity tomographic distribution image shown in FIG. 13A.

In FIG. 13A and FIG. 13B, measurement results obtained in condition with an average flow velocity is 1.0 micro meter per second are shown. FIG. 13A is a three-dimensional blood flow distribution tomography image, and FIG. 13B is a graph extracted from the three-dimensional blood flow distribution tomography image, showing a flow velocity distribution only at a position where X is 125 micron meters. In the present study, the dispersion error is 439 micron meters per second.

Figure 14:
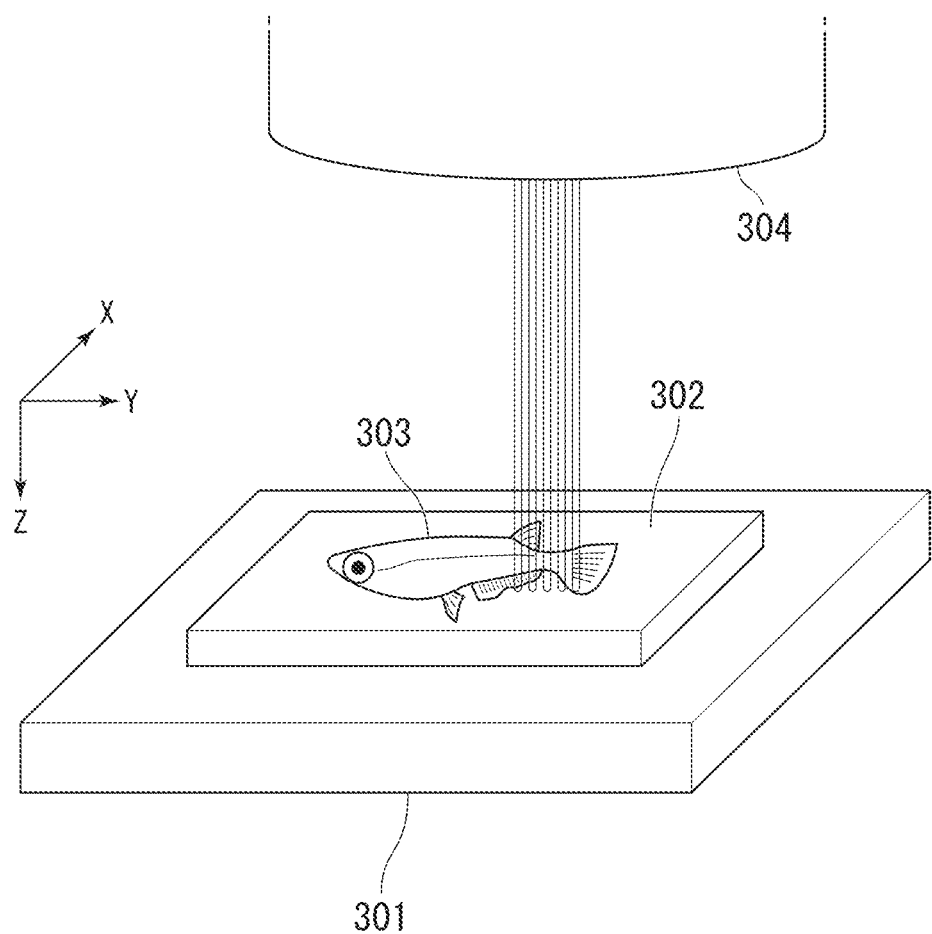
FIG. 14 is a schematic view showing an overview of a study using an Oryzias latipes.
Figure 15A:
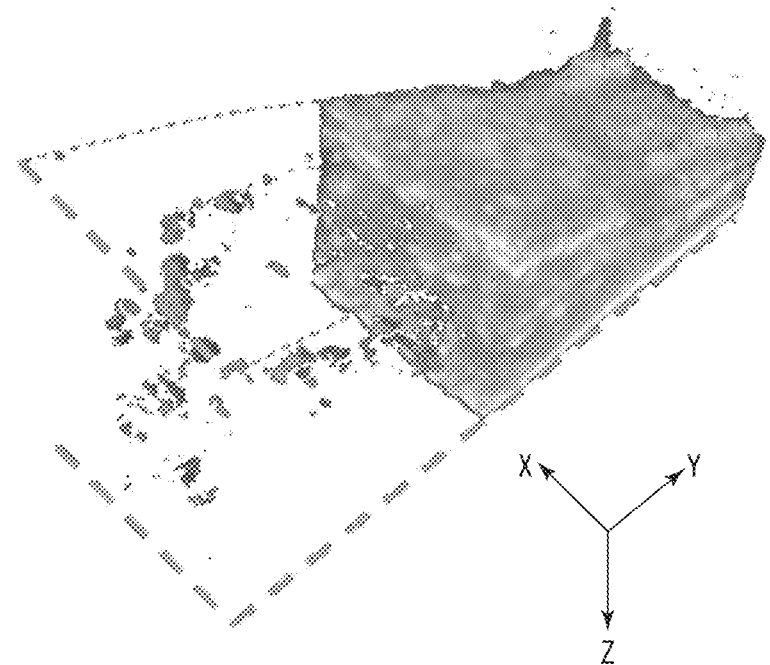
FIG. 15A is a view showing a three-dimensional blood flow velocity tomographic distribution image in the study using the Oryzias latipes.
Figure 15B:
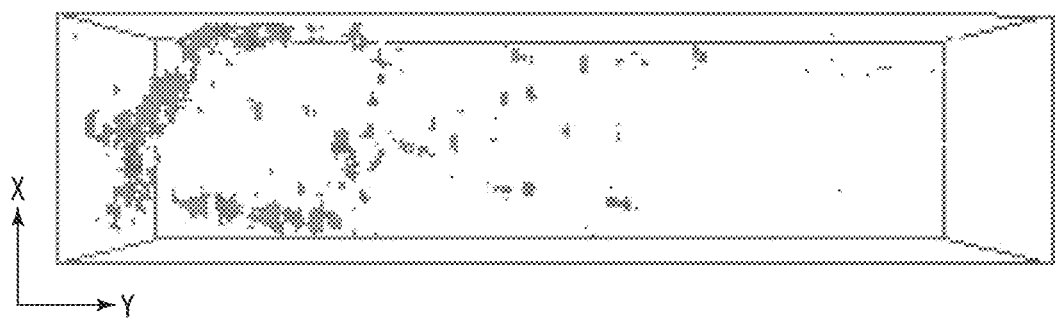
FIG. 15B is a view showing a three-dimensional blood flow velocity tomographic distribution image in the study using the Oryzias latipes.

In FIG. 14 to FIG. 15B, a summary and the measurement results of a study using Oryzias latipes are shown. As shown in FIG. 14, an Oryzias latipes 303 is put on a glass slide 302 disposed on a stage 301, then the object light is emitted from a distal end 304 of the object arm and irradiated on the Oryzias latipes 303 such that capillaries at a position near a caudal fin are measured.

FIG. 15A and FIG. 15B are three-dimensional blood flow velocity distribution tomography images. In FIG. 15A and FIG. 15B, a three-dimensional visualization of the capillaries meandering and crossing with each other, and a three-dimensional visualization of the Doppler frequency distribution of the blood flow velocity in the capillaries are shown.

Next, data obtained by measuring a blood flow velocity distribution in the human subcutaneous capillaries using the cancer invasiveness diagnosis system according to the present invention will be shown. A measurement region is set to be an inner side of the human forearm, and a measurement target is set to be a range from the skin surface to a position with a depth of approximately 500 micron meters.

Figure 16:
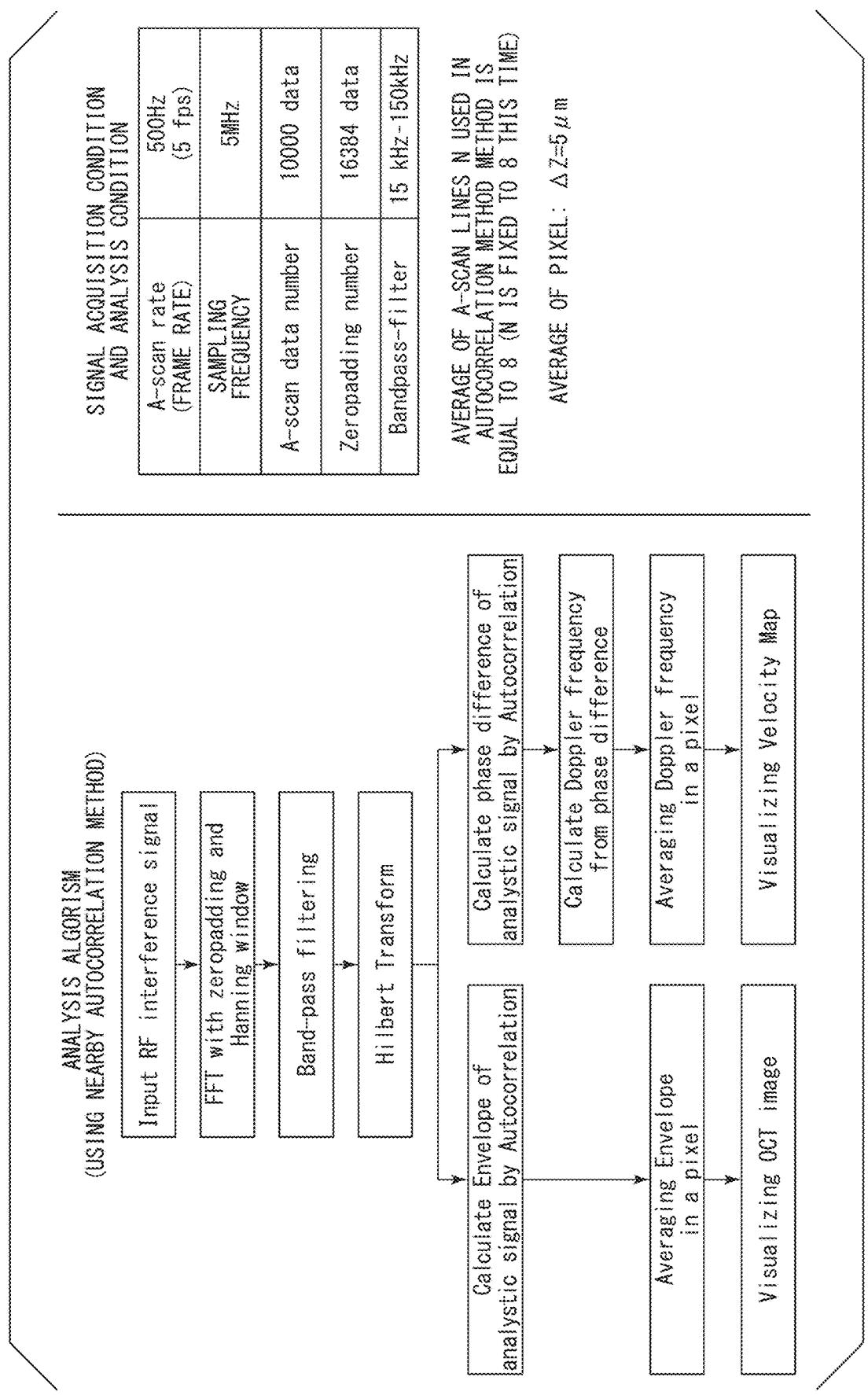
FIG. 16 is a view showing an example of an algorithm in the cancer invasiveness diagnosis system of the present invention.

The algorithm, signal acquisition conditions, and analysis conditions of the above-mentioned measurement are shown in FIG. 16. In the measurement, the common-phase noise is reduced by using the nearby autocorrelation method after the Hilbert transformation.

Figure 17:
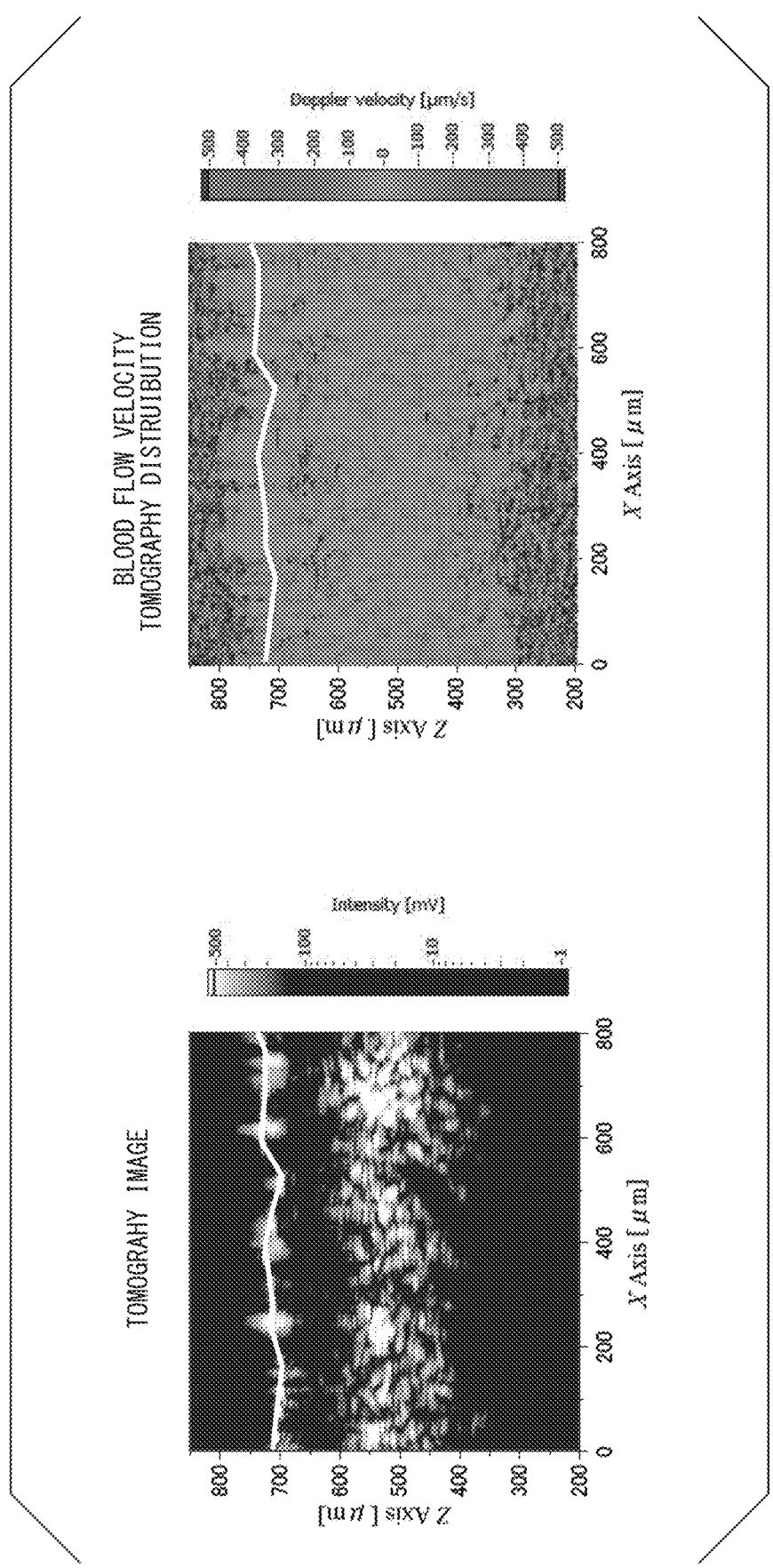
FIG. 17 is a view showing a measurement result of a blood flow velocity distribution in human subcutaneous blood capillaries.
Figure 18:
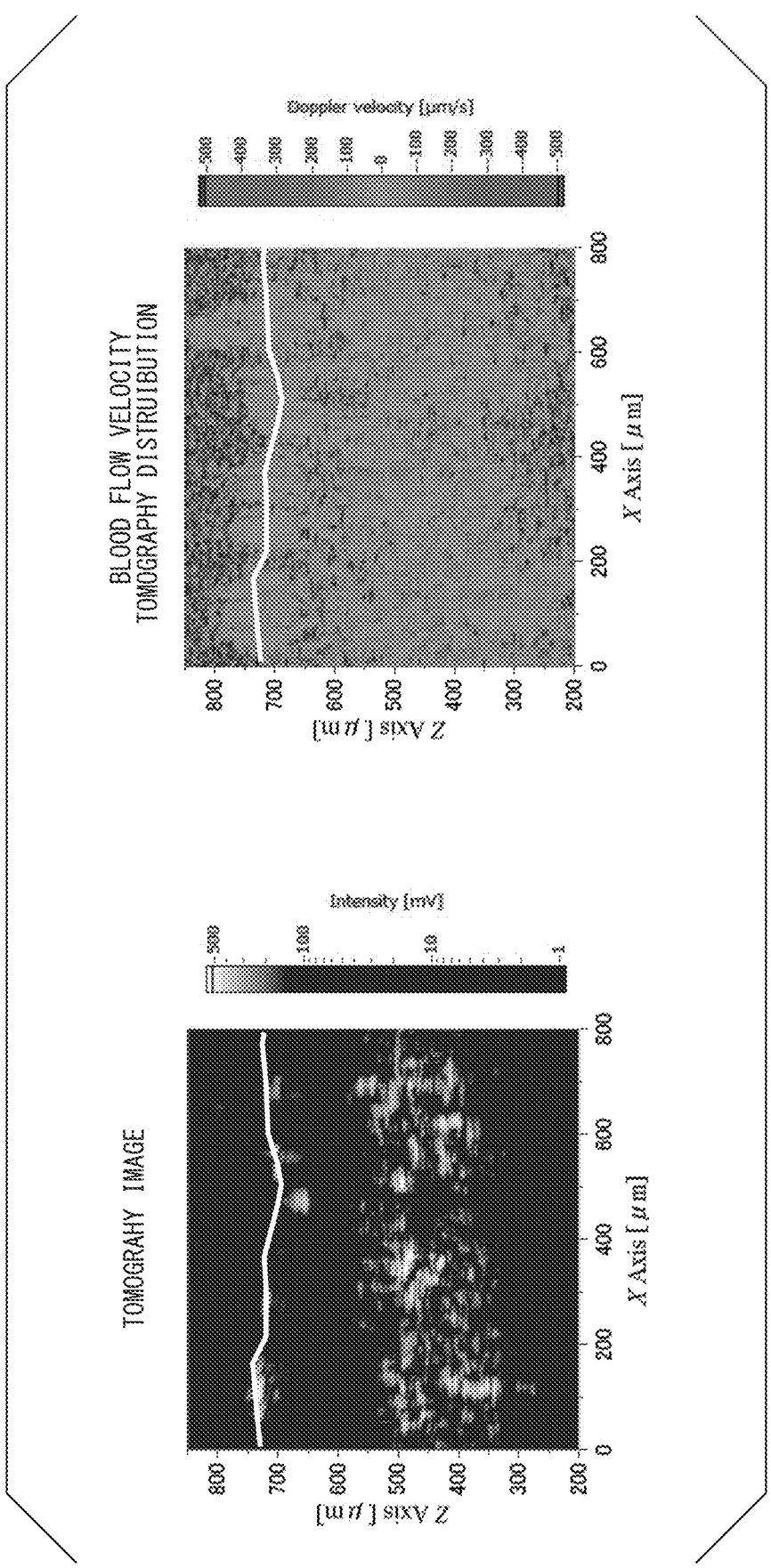
FIG. 18 is a view showing a measurement result of a blood flow velocity distribution in human subcutaneous blood capillaries (after applying a vasodilator).

Measurement results are shown in FIG. 17 and FIG. 18. In the FIG. 17 and FIG. 18, a tomography image is on the left, and a blood flow velocity distribution tomography image is on the right. In each of the tomography image and the blood flow velocity distribution tomography image, a white line is used for indicating a position of the skin surface.

In FIG. 17, a boundary portion between the epidermis and the dermis is shown at a position with a depth of approximately 100 micron meters from the skin surface (a position near 600 micron meters in the vertical axis (Z axis)). However, in the blood flow velocity distribution tomography image, images (black micro points) indicating the blood flow velocity in the capillaries are recognized near the boundary portion. In the present study, detection of a blood flow velocity equal to or lower than 200 micro meters per second is considered to be successful.

In FIG. 18, measurement results of applying the Methyl nicotinate (0.1 mass %) having the vasodilation function at the same region and then performing measurements after 5 minutes. Due to the vasodilation function of the Methyl nicotinate, an increase of the detected blood flow velocity images in the capillaries can be confirmed. According to the study, the blood flow velocity is increased to one and a half times that before the Methyl nicotinate is applied, and the area where the blood flow velocity is increased is significantly larger.

As described above, according to the cancer invasiveness diagnosis system of the present invention, it is confirmed that the blood flow velocity in the human capillaries can be tomographically visualized. The diameters of the capillaries just under the human epidermis are about 10 micro meters, which is considered to be the same level as the diameters of ends of the angiogenic blood vessels present in the cancer. Also, the blood flow velocity therein is considered to be the same level as that in the angiogenic blood vessels present in the cancer.

The degree of transparency just under the human epidermis is remarkably lower than that of the alimentary canal mucosa, and thus optical detection of the blood flow velocity in the human skin is more difficult. Accordingly, it is easier to optically visualize the blood flow velocity in the capillaries of the mucosa layer than to visualize of the blood flow velocity in the human subcutaneous capillaries. Thus, it is enough to affirm that a diagnosis of early-stage minimal cancer is sufficiently possible by a microtomography visualization of the blood flow velocity in the connected angiogenic blood vessels in the mucosa layer using the cancer invasiveness diagnosis system of the present invention.

The Methyl nicotinate used in the above-described study to the human subcutaneous capillaries is one of the vasodilators, and the usage of the Methyl nicotinate is intended to be an analogous reproduction of the existence state of the connected angiogenic blood vessels. The state in which the detected blood flow velocity increases after applying the Methyl nicotinate is similar with a state in which the connected angiogenic blood vessels exist in the gastrointestinal cancer, and thus detection of the former state can be regarded as an equivalent to identification and information acquisition of the connected angiogenic blood vessels.

Similar to the gastric walls, the esophagus and the colon's walls also have a submucosa layer and a muscularis propria layer. Accordingly, the cancer invasiveness diagnosis system of the present invention which is configured to specify and evaluate the connected angiogenic blood vessels is not only applicable to gastric cancer, but is also applicable to other gastrointestinal cancer such as esophageal cancer, colectoral cancer and the like.

Before the acquisition of the OCT tomography image, an intravenous administration of fine particles may be performed. Accordingly, instead of using red blood cells, the blood flow velocity information from the Doppler modulation signal of the fine particles flowing in the connected angiogenic blood vessels can be used. In blood vessels having a diameter of approximately 10 micron meters such as capillaries, a situation may occur in which red blood cells cannot smoothly flow such that it is difficult to obtain a Doppler signal. In such situations, occurrence of the Doppler modulation in the capillaries can be clearly seen. Nanoparticle having biocompatibility can be used as the fine particles, and a specific type of contrast agent that also includes fine particles can be used.

The cancer invasiveness determined by the cancer invasiveness diagnosis system of the present invention can be used as an index of a judgment of a cancer treatment effect after a vascularization inhibitor is applied.

The present invention also includes the following technical ideas.

(Supplemental Item 1)

A method of a lesion invasiveness determination, including:

emitting a low-coherence light on target tissue in which a target tumor is present to obtain an optical interference signal;

obtaining a tomography image of the target tissue having the target tumor and a blood flow velocity information in a blood vessel in the tomography image based on the optical interference signal; and determining the lesion invasiveness of the target tumor based on the tomography image and the blood flow velocity information.

(Supplemental Item 2)

The method of a lesion invasiveness determination according to the supplemental item 1, wherein the optical interference signal is obtained by emitting low-coherence light that is high-frequency modulated.

(Supplemental Item 3)

The method of a lesion invasiveness determination according to the supplemental item 1 or the supplemental item 2, wherein the blood flow velocity information includes information relating to an initial rise of the blood flow velocity due to a recovery of a blood flow after the blood vessel is pressed and the blood flow velocity in the blood vessel becomes equal to or lower than a predetermined value.

REFERENCE SIGNS LIST 1, 201 cancer invasiveness diagnosis system
10 microtomography probe
100, 200 endoscope
32 control calculation portion (determination portion)
Nv2 angiogenic blood vessels (connected angiogenic blood vessels)
Mp muscularis propria layer
St target tissue
Sm submucosa layer

What is claimed is:

1. A cancer invasiveness diagnosis system, comprising:
an endoscope;
a microtomography probe configured to be introduced into a body cavity together with the endoscope, the microtomography probe capable of emitting a low-coherence light on a target tissue in which a target tumor is present and obtaining an optical interference signal; and
a determination portion comprising a processor configured to obtain a tomography image of the target tissue including the target tumor and determine a blood flow velocity information of angiogenic blood vessels communicating with pre-existing capillaries in a mucosa layer from the tomography image based on the optical interference signal,
the determination portion being configured to determine a cancer invasiveness of the target tumor based on the tomography image and the blood flow velocity information by:
identifying connected angiogenic blood vessels communicating with pre-existing blood vessels in a submucosa layer or a muscularis propria layer having diameters larger than the angiogenic blood vessels communicating with pre-existing capillaries in the mucosa layer, based on the tomography image and the blood flow velocity information, and
determining the cancer invasiveness of the target tumor based on an evaluation result of the identified connected angiogenic blood vessels.

2. The cancer invasiveness diagnosis system according to claim 1, wherein the microtomography probe is capable of emitting the low-coherence light being high-frequency modulated.

3. The cancer invasiveness diagnosis system according to claim 1, wherein the endoscope and the microtomography probe are integrated and the microtomography probe comprises a pressing surface formed at an emission port and in a vicinity of the emission port of the microtomography probe, the pressing surface configured to press the target tissue in contact with the pressing surface, wherein
when the pressing surface is slightly in contact with the target tissue, the determination portion is configured to indicate positions of the connected angiogenic blood vessels from the blood flow velocity information of each blood vessel in the tomography image, and
when the pressing surface presses the target tissue while confirming the blood flow velocity information of the connected angiogenic blood vessels, until the blood flow velocity information of the connected angiogenic blood vessels is equal to or lower than a predetermined value such that ischemia occurs, and the pressing surface is operated to cancel the pressing to recover blood flow, the determination portion is configured to obtain the blood flow velocity information due to the recovery of the blood flow, the blood flow velocity information including information relating to an initial rise of the blood flow velocity information when the blood flow in the connected angiogenic blood vessels recovers.

* * * * *